(12) United States Patent
Delong et al.

(10) Patent No.: US 11,568,960 B2
(45) Date of Patent: Jan. 31, 2023

(54) NEURAL NETWORK ARCHITECTURES FOR SCORING AND VISUALIZING BIOLOGICAL SEQUENCE VARIATIONS USING MOLECULAR PHENOTYPE, AND SYSTEMS AND METHODS THEREFOR

(71) Applicant: Deep Genomics Incorporated, Toronto (CA)

(72) Inventors: Andrew Delong, Toronto (CA); Brendan Frey, Toronto (CA)

(73) Assignee: DEEP GENOMICS INCORPORATED, Toronto (CA)

(*) Notice: Subject to any disclaimer, the term of this patent is extended or adjusted under 35 U.S.C. 154(b) by 922 days.

(21) Appl. No.: 16/179,457

(22) Filed: Nov. 2, 2018

(65) Prior Publication Data
US 2019/0138878 A1 May 9, 2019

Related U.S. Application Data (63) Continuation of application No. PCT/CA2016/050776, filed on Jul. 4, 2016.
(Continued)

(51) Int. Cl.
*G16B 45/00* (2019.01)
*G06N 3/04* (2006.01)
(Continued)

(52) U.S. Cl.
CPC .......... *G16B 45/00* (2019.02); *G06N 3/002* (2013.01); *G06N 3/04* (2013.01); *G06N 3/084* (2013.01);
(Continued)

(58) Field of Classification Search
CPC ............ Y02A 90/10; G01N 33/6845; G01N 2500/10; G16B 30/00; G16B 30/10;
(Continued)

(56) References Cited

U.S. PATENT DOCUMENTS 10,185,803 B2 * 1/2019 Frey ................ G16B 40/00
11,183,271 B2 * 11/2021 Frey ................ G16B 40/00
(Continued)

FOREIGN PATENT DOCUMENTS

WO WO-2016201564 A1 * 12/2016 ............ G16B 40/20
WO WO-2017193198 A 11/2017

OTHER PUBLICATIONS

Frenz, C. (2005) Neural Network-Based Prediction of Mutation-Induced Protein Stability Changes in Staphylococcal Nuclease at 20 Residue Positions. Proteins: Structure Function and Bioinformatics, 59:147-151. (Year: 2005).*
(Continued)

*Primary Examiner* — Mary K Zeman
(74) *Attorney, Agent, or Firm* — Wilson Sonsini Goodrich & Rosati (57) ABSTRACT

Systems and methods for scoring and visualizing the effects of variants in biological sequences. Variants may include substitutions, insertions and deletions. The method comprises encoding biological sequences as vector sequences and then operating a neural network in the forward-propagation mode and possibly in the back-propagation mode to compute variant scores. Variant scores are determined by normalizing the gradients. Variant scores may be used to select a subset of variants, which are then used to produce modified vector sequences which are analyzed by the neural network operating in forward-propagation mode, to determine improved variant scores. The variant scores may be visualized using black and white, greyscale or colored elements that are arranged in blocks with dimensions corresponding to different possible symbols and the length of the sequence. These blocks are aligned with the biological sequence, which is illustrated by a symbol sequence arranged in a line.

18 Claims, 6 Drawing Sheets

Specification includes a Sequence Listing.

Related U.S. Application Data (60) Provisional application No. 62/335,810, filed on May 13, 2016.

(51) Int. Cl.

| | | |
|---|---|---|
| *G16B 40/00* | (2019.01) | |
| *G16B 40/20* | (2019.01) | |
| *G06N 3/00* | (2006.01) | |
| *G06N 3/08* | (2006.01) | |
| *G06N 5/04* | (2006.01) | |
| *G16B 99/00* | (2019.01) | |
| *C12Q 1/6827* | (2018.01) | |
| *C12Q 1/68* | (2018.01) | |

(52) U.S. Cl.
CPC ............. *G06N 5/046* (2013.01); *G16B 40/00* (2019.02); *G16B 40/20* (2019.02); *G16B 99/00* (2019.02); *C12Q 1/68* (2013.01); *C12Q 1/6827* (2013.01)

(58) Field of Classification Search
CPC ........ G16B 20/00; G16B 40/00; G16B 30/20; G16B 40/20; G16B 20/20; G16B 20/30; G16B 15/00; G16B 25/10; G16B 35/00; G16B 5/00; G16B 20/40; G16B 35/20; G16B 45/00; G16B 5/20; G16B 50/00; G16B 50/20; G16B 50/30; G16B 99/00; G16C 20/60; G16C 20/64; G16C 20/00; G06N 3/084; G06N 3/08; G06N 3/0454; G06N 3/04; G06N 3/0481; G06N 7/005; G06N 3/0445; G06N 5/046; G06N 3/082; G06N 20/00; G06N 20/10; G16H 70/60; G16H 10/40; G16H 50/70; G06K 9/6267; G06K 9/6228; G06K 9/6232; G06K 9/6255; G06K 9/6256
See application file for complete search history.

(56) References Cited

U.S. PATENT DOCUMENTS

| | | | | |
|---|---|---|---|---|
| 2007/0166707 A1* | 7/2007 | Schadt | ................. | C12Q 1/6883 435/6.11 |
| 2014/0280327 A1 | 9/2014 | Pham et al. | | |
| 2015/0004158 A1* | 1/2015 | Shipp | ............... | G01N 33/57484 424/133.1 |
| 2018/0107927 A1* | 4/2018 | Frey | ...................... | G16B 40/00 |
| 2018/0165412 A1* | 6/2018 | Frey | ...................... | G16B 30/00 |
| 2019/0138878 A1* | 5/2019 | Delong | .................. | G16B 40/20 |
| 2019/0220740 A1* | 7/2019 | Xiong | .................... | G16H 50/70 |

OTHER PUBLICATIONS

Qi, Y. et al. (2012) A Unified Multitask Architecture for Predicting Local Protein Properties. PLOS One 7:3 e32235, 11 pages. (Year: 2012).*

Zhou, J. et al. (2015) Predicting effects of noncoding variants with deep learning-based sequence model. Nature Methods 12:10, p. 931-938. (Year: 2015).*

Manning et al. Biologically inspired intelligent decision making: a commentary on the use of artificial neural networks in bioinformatics (2014) Bioengineered 5:2 80-95. (Year: 2014).*

Shrikumar et al. Not just a black box: learning important features through propagating activation differences. Version 2, deposited May 8, 2016, arXiv: 1605.01713v2. (Year: 2016).*

Adetiba et al. Lung cancer prediction using neural network ensemble with histogram of oriented gradient genomic features. 2015 The Scientific World Journal ID: 786013, 17 pages. (Year: 2015).*

Blasiak et al. a family of feed-forward models for protein sequence classification. (2012) IN: Flach et al (eds) ECML PKDD2012 Part II, LCNS 7524, p. 419-434, Springer-Verlag, Berlin. (Year: 2012).*

Exam Report issued in European Application No. 16901179.8 dated Apr. 16, 2021.

Ciuca, et al. On the Irrelevant Feature Discarding in Neural Networks and its Applications in Medicine. Studies in Health Technology and Informatics (1996): 965-969.

EP16901179.8 the Extended European Search Report dated Nov. 29, 2019.

International search report dated Mar. 6, 2017 for PCT Application No. PCT/CA2016/050776.

Yan, et al. Prediction of mutation positions in H5N1 neuraminidases from influenza A virus by means of neural network. Annals of biomedical engineering 38.3 (2010): 984-992.

Yeung, et al. Principles of sensitivity analysis. Sensitivity analysis for neural networks. Springer, Berlin, Heidelberg, 2009. 17-24.

Exam Report issued in Canadian Patent Application No. 3,024,017 dated May 19, 2022.

Further Examination Report issued in European Patent Application No. 16901179.8 dated Mar. 9, 2022.

* cited by examiner

SEQUENCE LISTING

<160> NUMBER OF SEQ ID NOS: 1

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgtacgtac gtacgt                                                    16

NEURAL NETWORK ARCHITECTURES FOR SCORING AND VISUALIZING BIOLOGICAL SEQUENCE VARIATIONS USING MOLECULAR PHENOTYPE, AND SYSTEMS AND METHODS THEREFOR

SEQUENCE LISTING

The instant application contains a Sequence Listing which has been submitted electronically in ASCII format and is hereby incorporated by reference in its entirety. Said ASCII copy, created on Apr. 28, 2022, is named 51110-704_301_SL.txt and is 684 bytes in size.

TECHNICAL FIELD

The following relates generally to the field of genetic variant analysis and the field of neural network architectures, and more particularly to scoring and visualizing the effects of variations in biological sequences using neural networks that relate biological sequences and molecular phenotypes.

BACKGROUND

Precision medicine, genetic testing, therapeutic development, patient stratification, patient-patient networking and whole genome, exome and gene panel analysis require systems and method that can accurately score and visualize biological sequence variations that are important functionally, such as in causing or contributing to a disease or disorder.

Biological sequence variants, also called variants, impact function by altering molecular phenotypes, which are aspects of biological molecules that participate in biochemical processes and in the development and maintenance of human cells, tissues, and organs.

Most existing methods for genome or DNA sequence analysis are suited to mutations in exons that either change an amino acid in a protein or prevent the production of the protein; to mutations that directly degrade splice sites very close to exon boundaries; or to mutations that are in conserved sequence regions. Most existing methods for protein sequence analysis are suited to mutations that modify binding domains; or to mutations that are in conserved sequence regions.

Over the past decade, the importance of developing methods that are more generally useful in identifying and visualizing genomic variations has been underscored by several observations: Most existing methods narrowly focus on exons, but evolution is estimated to preserve at least 5.5% of the human genome and only 1% accounts for exons within genes; biological complexity relies on regulatory elements encoded in the genome and cannot be accounted for simply by the gene library (e.g., balsam poplar trees have twice as many genes as humans); differences between organisms rely on differences on regulatory elements encoded in the genome and cannot be accounted for by differences between genes alone (e.g., less than 1% of human genes are distinct from those of mice and dogs); increasingly, disease-causing variants have been found outside of exons, indicating that crucial information is encoded outside of those sequences.

These observations have led to explorations into how biological sequence variations cause changes in what are often referred to as molecular phenotypes. Molecular phenotypes correspond to aspects of physical molecules that play roles, such as in human cells, tissues, organs. Examples include the strength of binding between a protein and a DNA sequence; the strength of interaction between two proteins; the fraction of mRNA transcripts in a particular tissue that contain a particular exon; DNA curvature structure; DNA methylation patterns; RNA folding interactions; and inter-cell signalling. Molecular phenotypes can be quantified in a variety of ways, such as by a vector of one or more real-valued numbers, or by a probability distribution.

The systems and methods described herein can be used to score and visualize biological sequence variations using neural networks that relate biological sequences to molecular phenotypes.

SUMMARY

In one aspect, a method for determining a variant score for each of at least one substitution variant at each of one or more positions in a reference biological sequence using a molecular phenotype neural network (MPNN) Is provided, the reference biological sequence characterized by a sequence of reference symbols, the method comprising: obtaining at an input layer of the MPNN the reference biological sequence; obtaining at least one substitution variants, each substitution variant associated with a position in the reference biological sequence; operating the MPNN in a forward-propagation mode to determine the molecular phenotype for the reference biological sequence; operating the MPNN in the back-propagation mode to determine the gradients for each of the at least one substitution variants and for each of the at least one substitution variants the gradient for the reference symbol at the respective position in the reference biological sequence; and for each of the at least one substitution variants, setting a variant score by comparing, at a comparator, the gradient for the variant and the gradient for the reference symbol at the respective variant position.

The reference biological sequence may be encoded by an encoder prior to operation of the MPNN, the encoder generating a reference vector sequence encoding the reference biological sequence.

The comparing may comprise subtracting the gradient for the reference symbol at the variant position from the gradient for the substitution variant.

Setting a variant score may further comprise, for each of the one or more substitution variants, if the variant score is greater than a pre-determined threshold: obtaining a variant biological sequence representing the reference biological sequence modified by the substitution variant at the associated position in the reference biological sequence; operating the MPNN in the forward-propagation mode to determine the molecular phenotype for the variant biological sequence; wherein the setting the variant score further comprises comparing the molecular phenotype for the variant biological sequence and the molecular phenotype for the reference biological sequence.

The comparing may comprise subtracting the molecular phenotype for the reference biological sequence from the molecular phenotype for the variant biological sequence.

Operating the MPNN in the back-propagation mode to determine the gradients may comprise comparing the output of the MPNN to a measured target.

The setting a variant score may further comprise obtaining an absolute value of the comparison.

The setting a variant score may further comprise: determining the variant scores for all substitution variants at the associated position in the reference biological sequence; and dividing the a variant score by the maximum absolute value of the variant scores for all substitution variants at the associated position in the reference biological sequence.

The setting a variant score may comprise setting the variant score to a value that is obtained by operating a scoring module neural network in feed-forward mode, wherein the input of the scoring module neural network comprises: the gradient for the substitution variant and the gradients for all other symbols at the variant position in the reference biological sequence; the reference biological sequence; and the molecular phenotype.

In another aspect, a method for visualizing numerical variant scores for at least one substitution, insertion or deletion variants at each of one or more positions in a reference biological sequence of length n and of alphabet size m is provided, the method comprising: illustrating the reference biological sequence by arranging the n symbols along a first row; and illustrating variant scores for variants as additional rows of n elements of visually distinctive elements aligned with the first row, each additional row encoding the numerical values of the variant scores.

Illustrating substitution variants may comprise generating a m×n matrix of visually distinctive elements.

Illustrating insertion variants may comprise generating a m×n matrix of visually distinctive elements.

Illustrating deletion variants may comprise generating a 1×n matrix of visually distinctive elements.

The visually distinctive elements may comprise black and white, greyscale, or color elements.

In a further aspect, a system for determining a variant score for each of at least one substitution variant at each of one or more positions in a reference biological sequence is provided, the reference biological sequence characterized by a sequence of reference symbols, the system comprising: a module configured to obtain a reference biological sequence and at least one substitution variants, each substitution variant associated with a position in the reference biological sequence; a molecular phenotype neural network (MPNN) configured to determine a molecular phenotype for a biological sequence, the MPNN having an input layer configured to obtain the biological sequence and one or more feature detectors configured to determine the molecular phenotype, the MPNN further configured to operate in a back-propagation mode to determine the molecular phenotype gradients for the at least one substitution variants and for each of the at least one substitution variants the gradient for the reference symbol at the respective position in the reference biological sequence; a comparator for setting a variant score for each of the at least one variant by comparing the gradient for the variant and the gradient for the reference symbol at the respective variant position in the reference biological sequence.

The system may further comprise an encoder to encode the reference biological sequence prior to operation of the MPNN, the encoder generating a reference vector sequence encoding the reference biological sequence.

The comparing may comprise subtracting the gradient for the reference symbol at the variant position from the gradient for the substitution variant.

The comparator may be further configured to, for each of the one or more substitution variants, if the variant score is greater than a pre-determined threshold: obtain a variant biological sequence representing the reference biological sequence modified by the substitution variant at the associated position in the reference biological sequence; operate the MPNN in the forward-propagation mode to determine the molecular phenotype for the variant biological sequence; compare the molecular phenotype for the variant biological sequence and the molecular phenotype for the reference biological sequence.

The comparator may further subtract the molecular phenotype for the reference biological sequence from the molecular phenotype for the variant biological sequence.

The back-propagation mode may comprise comparing the output of the MPNN to a measured target.

The comparator setting the variant score may comprise obtaining an absolute value of the comparison.

The comparator setting the variant score may further comprise: determining the variant scores for all substitution variants at the associated position in the reference biological sequence; and dividing the a variant score by the maximum absolute value of the variant scores for all substitution variants at the associated position in the reference biological sequence.

The comparator setting the variant score may comprise setting the variant score to a value that is obtained by operating a scoring module neural network in feed-forward mode, wherein the input of the scoring module neural network comprises: the gradient for the substitution variant and the gradients for all other symbols at the variant position in the reference biological sequence; the reference biological sequence; and the molecular phenotype.

In yet another aspect, a system for visualizing numerical variant scores for at least one substitution, insertion or deletion variants at each of one or more positions in a reference biological sequence of length n and of alphabet size m is provided, the system comprising a processor, a memory and a display, the memory storing computer instructions which, when executed by the processor, cause the processor to depict on the display: the reference biological sequence by arranging the n symbols along a first row; and variant scores for variants as additional rows of n elements of visually distinctive elements aligned with the first row, each additional row encoding the numerical values of the variant scores.

Illustrating substitution variants may comprise generating a m×n matrix of visually distinctive elements.

Illustrating insertion variants may comprise generating a m×n matrix of visually distinctive elements.

Illustrating deletion variants may comprise generating a 1×n matrix of visually distinctive elements.

The visually distinctive elements may comprise black and white, greyscale, or color elements.

These and other aspects are contemplated and described herein. It will be appreciated that the foregoing summary sets out representative aspects of methods and systems for producing an expanded training set for machine learning using biological sequences to assist skilled readers in understanding the following detailed description.

DESCRIPTION OF THE DRAWINGS

The features of the invention will become more apparent in the following detailed description in which reference is made to the appended drawings wherein:

FIG. 4 discloses SEQ ID NO: 1.

FIG. 6 discloses SEQ ID NO: 1.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

A key unmet need in precision medicine is the ability to automatically or semi-automatically analyze biological sequence variants by examining their impact on molecular phenotypes. Biological sequence variants, also called variants, impact function by altering molecular phenotypes, which are aspects of biological molecules that participate in biochemical processes and in the development and maintenance of human cells, tissues, and organs.

A biological sequence variant, also called a variant, is a biological sequence, such as a DNA sequence, an RNA sequence or a protein sequence, that may be derived from an existing biological sequence through a combination of substitutions, insertions and deletions. For example, the gene BRCA1 is represented as a specific DNA sequence of length 81,189 in the reference genome. If the samples from multiple patients are sequenced, then multiple different versions of the DNA sequence for BRCA1 may be obtained. These sequences, together with the sequence from the reference genome, form a set of variants. As another example, all single nucleotide substitution variants of the DNA sequence for BRCA1 comprise 243,567 variants: three possible substitutions for each nucleotide times 81,189 nucleotides.

To distinguish variants that are derived from the same biological sequence from those that are derived from different biological sequences, the following will refer to variants that are derived from the same biological sequence as "biologically related variants" and the term "biologically related" is used as an adjective to imply that a variant is among a set of biologically related variants. For example, the variants derived from the gene BRCA1 are biologically related variants. The variants derived from another gene, SMN1, are also biologically related variants. However, the variants derived from BRCA1 are not biologically related to the variants derived from SMN1. The term "biologically related variants" is used to organize variants according to their function, but it will be appreciated that this organization may be different according to different functions. For example, when they are transcribed, two different but homologous genes may generate the same RNA sequence. Variants in the RNA sequence may impact function in the same way, such as by impacting RNA stability. This is the case even though they originated from two different, albeit homologous, DNA sequences. The RNA sequence variants, regardless of from which gene they came, may be considered to be biologically related.

Biologically related variants may be derived naturally by DNA replication error; by spontaneous mutagenesis; by sexual reproduction; by evolution; by DNA, RNA and protein editing/modification processes; by retroviral activity, and by other means. Biologically related variants may be derived experimentally by plasmid construction, by gene editing systems such as CRISPR/Cas9, by sequencing samples from patients and aligning them to a reference sequence, and by other means. Biologically related variants may be derived computationally by applying a series of random or preselected substitutions, insertions and deletions to a reference sequence, by using a model of mutation to generate variants, and by other means. Biologically related variants may be derived from a DNA or RNA sequence of a patient, a sequence that would result when a DNA or RNA editing system is applied, a sequence where nucleotides targeted by a therapy are set to fixed values, a sequence where nucleotides targeted by a therapy are set to values other than existing values, or a sequence where nucleotides that overlap, fully or partially, with nucleotides that are targeted by a therapy are deactivated. It will be appreciated that there are other ways in which biologically related variants may be produced.

Depending on the function being studied, different sets of biologically related variants may be obtained from the same biological sequences. In the above example, DNA sequences for the BRCA1 gene of length 81,189 may be obtained from the reference genome and a group of patients and form a set of biologically related variants. As an example, if we are interested in how variants impact splicing of exon 6 in BRCA1, for each patient and the reference genome, we may extract a subsequence of length 600 nucleotides centered at the 3 prime end of exon 6. These splice site region sequences would form a different set of biologically related variants than the set of whole-gene biologically related variants.

The above discussion underscores that the functional meaning of a variant is context dependent, that is, dependent on the conditions. Consider the reference genome and an intronic single nucleotide substitution located 100 nucleotides from the 3 prime splice site of exon 6 in the BRCA1 gene. We can view this as two BRCA1 variants of length 81,189 nucleotides, or as two exon 6 splice site region variants of length 600 nucleotides, or, in the extreme, as two chromosome 17 variants of length 83 million nucleotides (BRCA1 is located on chromosome 17). Viewing the single nucleotide substitution in these three different situations would be important for understanding its impact on BRCA1 gene expression, BRCA1 exon 6 splicing, and chromatin interactions in chromosome 17. Furthermore, consider the same single nucleotide substitution in two different patients. Because the neighbouring sequence may be different in the two patients, the variants may be different.

A variant impacts function by altering one or more "molecular phenotypes", which quantify aspects of biological molecules that participate in the biochemical processes that are responsible for the development and maintenance of human cells, tissues, and organs. A "molecular phenotype" may be a quantity, level, potential, process outcome, or qualitative description. The term "molecular phenotype" may be used interchangeably with the term "cell variable". Examples of molecular phenotypes include the concentration of BRCA1 transcripts in a population of cells; the percentage of BRCA1 transcripts that include exon 6; chromatin contact points in chromosome 17; the strength of binding between a DNA sequence and a protein; the strength of interaction between two proteins; DNA methylation patterns; RNA folding interactions; and inter-cell signalling. A molecular phenotype can be quantified in a variety of ways, such as by using a categorical variable, a single numerical value, a vector of real-valued numbers, or a probability distribution.

A variant that alters a molecular phenotype is more likely to alter a gross phenotype, such as disease or aging, than a variant that does not alter any molecular phenotype. This is because variants generally impact gross phenotypes by altering the biochemical processes that rely on DNA, RNA and protein sequences.

Since variants impact function by altering molecular phenotypes, a set of biologically related variants can be associated with a set of molecular phenotypes. BRCA1 whole-gene variants may be associated with the molecular phenotype measuring BRCA1 transcript concentration. BRCA1 exon 6 splice site region variants may be associated with the molecular phenotype measuring the percentage of BRCA1 transcripts that include exon 6. Chromosome 17 variants may be associated with the molecular phenotype measuring chromatin contact points in chromosome 17. This association may be one to one, one to many, many to one, or many to many. For instance, BRCA1 whole-gene variants, BRCA1 exon 6 splice region variants and chromosome 17 variants may be associated with the molecular phenotype measuring BRCA1 transcript concentration.

The association of a variant with a molecular phenotype does not imply for certain that the variant alters the molecular phenotype, it only implies that it may alter the molecular phenotype. An intronic single nucleotide substitution located 100 nucleotides from the 3 prime splice site of exon 6 in the BRCA1 gene may alter the percentage of BRCA1 transcripts that include exon 6, whereas a single nucleotide substitution located 99 nucleotides from the 3 prime splice site of exon 6 in the BRCA1 gene may not. Also, for the former case, whereas a G to T substitution may alter the molecular phenotype, a G to A substitution may not. Furthermore, the molecular phenotype may be altered in one cell type, but not in another, even if the variant is exactly the same. This is another example of context dependence.

There are different approaches to determining how biologically related variants alter molecular phenotypes, ranging from experimental, to computational, to hybrid approaches.

The systems and methods described herein can be used to score and visualize the effects of biological sequence variants using neural networks that relate biological sequences to molecular phenotypes.

The present systems comprise structured computational architectures referred to herein as molecular phenotype neural networks (MPNNs). MPNNs are artificial neural networks, also called neural networks, which are a powerful class of architectures for applying a series of computations to an input so as to determine an output. The input to the MPNN is used to determine the outputs of a set of feature detectors, which are then used to determine the outputs of other feature detectors, and so on, layer by layer, until the molecular phenotype output is determined. An MPNN architecture can be thought of as a configurable set of processors configured to perform a complex computation. The configuration is normally done in a phase called training, wherein the parameters of the MPNN are configured so as to maximize the computation's performance on determining molecular phenotypes or, equivalently, to minimize the errors made on that task. Because the MPNN gets better at a given task throughout training, the MPNN is said to be learning the task as training proceeds. MPNNs can be trained using machine learning methods. Once configured, an MPNN can be deployed for use in the task for which it was trained and herein for linking variants as described below.

The following provides systems and methods for scoring the effects of biological sequence variants efficiently and accurately by providing useful information about how different symbols or combinations of symbols in biological sequences affect the molecular phenotype and/or a loss function that depends on the molecular phenotype. The systems comprise MPNNs that have inputs comprising biological sequences and produce outputs comprising molecular phenotypes. The degree to which biological sequence variations produce changes in the ascertained molecular phenotypes is used to score and visualize the variants.

The methods and systems use molecular phenotype neural networks operating in the forward-propagation mode to take as input biological sequences and to output molecular phenotypes, and operate the neural networks in back-propagation mode to determine gradients, which are processed by a scoring module to score variations in biological sequences.

With regard to scoring sequence variants, the method can improve the computational efficiency of the scoring process, and the accuracy of the scores themselves. With regard to visualizing variant scores, the method introduces computational and design aspects that can improve the user experience. The input to the neural network comprises a biological sequence, such as a DNA sequence, an RNA sequence or an amino acid sequence. We denote a biological sequence by S and the symbol at position i by $s_i$. Each symbol in the sequence comes from an alphabet $\mathcal{A}$, that is, $s_i \in \mathcal{A}$. For DNA, each symbol comes from the alphabet $\mathcal{A} = \{A,C,G,T\}$; for RNA, the alphabet is $\mathcal{A} = \{A,C,G,U\}$; and for protein sequences, the alphabet is $\mathcal{A} = \{A, C, D, E, F, G, H, I, K, L, M, N, P, Q, R, S, T, V, W, Y\}$. We use m to denote the number of symbols in the alphabet and a to denote the symbols, so that $\mathcal{A} = \{\alpha_1, \ldots \alpha_m\}$.

It will be appreciated by those skilled in the art that there may be other inputs to the neural network, such as specifications of cell types, diseases, environmental factors and biochemical factors. These other inputs may be held constant when determining the variant scores using the methods and systems described herein, in which case the variant scores are context-dependent. The other inputs can be varied to determine how the variant scores depend on them.

The methods and systems described herein are used to score biologically related variants. When it is necessary to distinguish a modified biological sequence from its original biological sequence, we will refer to the latter as a reference biological sequence or a reference sequence. The symbols in these sequences are referred to as reference symbols.

Variants may include substitutions, deletions, insertions and combinations of these; rare and common variants; and variants derived from different sources. A substitution is the replacement of an element in a biological sequence with a different element; a deletion is the removal of an element from a biological sequence, such that the modified sequence becomes shorter; an insertion is the addition of an element at a particular location in the biological sequence, such that the modified sequence becomes longer. We will refer to the score associated with a variant as a variant score, but in some cases, to specify the type of variant, we will use a term such as substitution score, deletion score or insertion score. The type of variant will often not be explicitly described, but will be evident to a person of skill from the applicant at hand.

In the case of substitutions, the modified symbols that arise from the substitutions are referred to as variants. Each of these variants has a corresponding reference symbol.

For example, consider a reference DNA sequence CAAGTTT of length n=7 and with an alphabet $\mathcal{A} = (A, C, G, T)$, such that m=4. The reference symbol at position 4 is G. For the case of substitutions, there are three possible variants at position 4: A, C, T.

Figure 1:
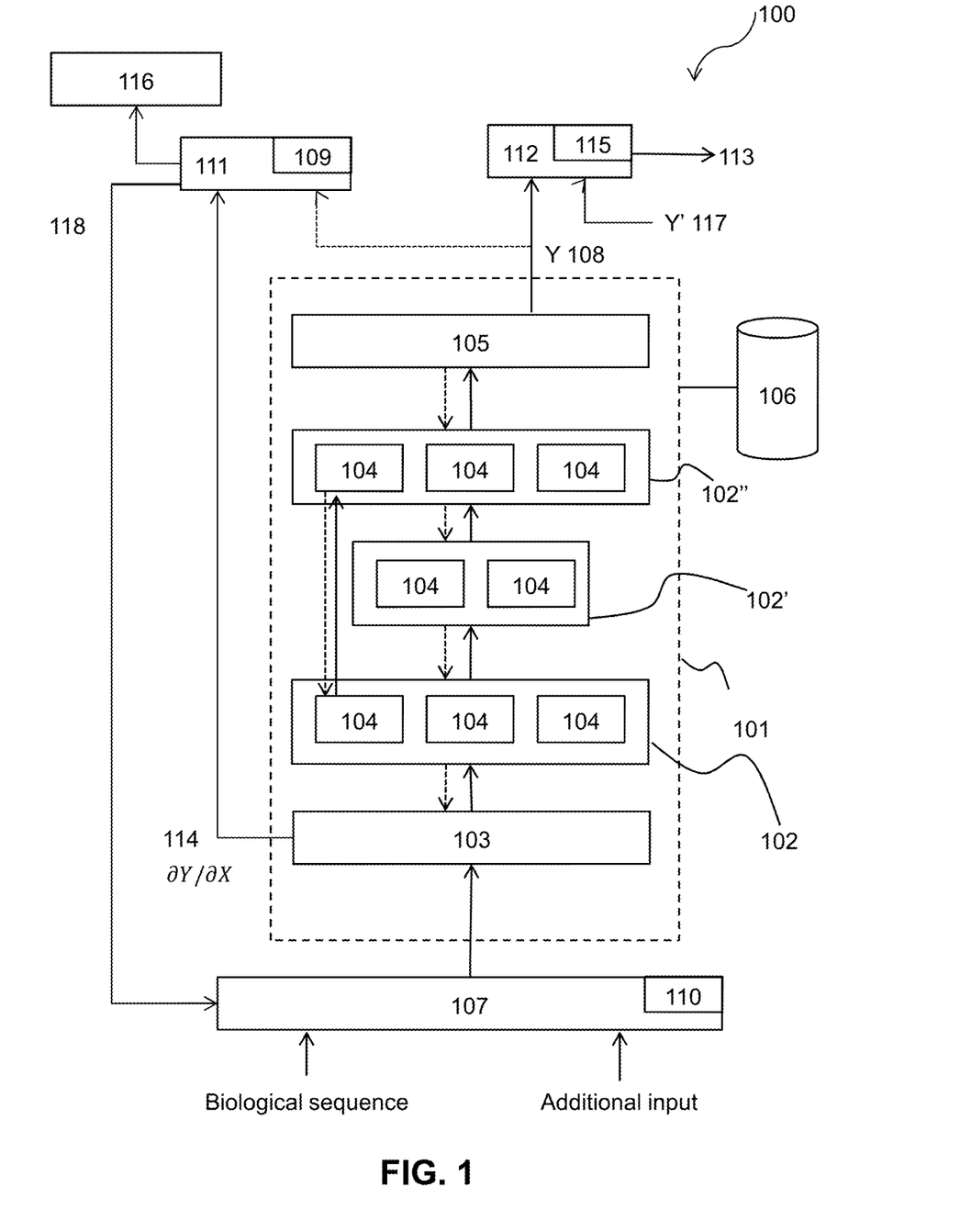
FIG. 1 is a block diagram illustrating an embodiment of a system for scoring and visualizing biological sequence variations.

Referring now to FIG. 1, a system (100) comprises an MPNN (101) that is a neural network comprising a layer of input values that represents the variant (103) (which may be referred to as an "input layer"), one or more layers of feature detectors (102, 102', 102") and a layer of output values that represents the molecular phenotype (105) (which may be referred to as an "output layer"). Each layer of feature detectors (102, 102', 102") comprises one or more feature detectors (104), wherein each feature detector comprises or is implemented by a processor. Weights may be applied in each feature detector (104) in accordance with learned weighting, which is generally learned in a training stage of the neural network. The input values, the learned weights, the feature detector outputs and the output values may be stored in a memory (106) linked to the MPNN (101).

It will be appreciated that there are many types of neural network that may be used in the embodiments described herein, including, but not limited to: feedforward neural networks, autoencoders, multi-task neural networks, recurrent neural networks, radial basis function networks, Kohonen self-organizing networks, learning vector quantization networks, modular neural networks and long short-term memory neural networks. It will also be appreciated that many different machine learning architectures can be represented as neural networks, including, but not limited to: linear regression, logistic regression, softmax regression, decision trees, random forests and support vector machines. Differences between techniques and architectures often pertain to differences in the cost functions and optimization procedures used to configure the architecture using a training set.

The particular MPNN (101) shown in FIG. 1 is an example architecture; the particular links between the feature detectors (104) may differ in various embodiments, which are not all depicted in the figures. A person of skill in the art would appreciate that such embodiments are contemplated herein.

The MPNN (101) may be operated in one or the other or both of two modes: the forward-propagation mode and the back-propagation mode. In the forward-propagation mode, the MPNN takes as input X, applies a series of computations resulting in intermediate values Z, and then applies computations to ascertain the output Y. The quantities X, Y and Z may each be a scalar value, a vector of values, or a set of values. The MPNN is configurable and its configuration is represented by parameters $W=(w_1, \ldots, w_p)$, where p is the number of parameters. For any choice of configuration W, denote the output Y ascertained by the neural network by $Y=F(X;W)$, where F defines the 'architecture' of the MPNN. As shown in the system depicted in FIG. 1, the input X to the MPNN comprises a biological sequence, which may be a reference sequence or a variant and the output Y represents a molecular phenotype or a set of molecular phenotypes, which may or may not be condition-specific. It will be appreciated that the input may include additional information, which may comprise, for example, environmental factors, cell labels, tissue labels, disease labels, and other relevant inputs.

In the forward-propagation mode, each layer (102, 102', 102") of feature detectors comprises the structured determination of the output of the feature detectors (104), and each feature detector (104) implements a computation that maps an input to an output. The feature detectors (104) in a layer accept a plurality of inputs from previous layers, combine them with a subset of weights, or parameters, W, and apply activation functions. Generally, the output of a feature detector in layer l may be provided as input to one or more feature detectors in layers l+1, l+2, . . . , L, where L is the number of layers of feature detectors. For example, in FIG. 1, outputs of feature detectors (104) of layer (102) may be provided as input to one or more feature detectors (104) of a plurality of subsequent layers (102' and 102"), as shown by the solid arrows.

One or more feature detectors (104) may be implemented by processing hardware, such as a single or multi-core processor and/or graphics processing unit(s) (GPU(s)). Further, it will be understood that each feature detector (104) may be considered to be associated with an intermediate computation or an input of the neural network for an intermediate layer or an input layer, respectively. The use of large (many intermediate computations) and deep (multiple layers of computations) neural networks may improve the predictive performances of the MPNN compared to other systems.

It may be advantageous for the system to comprise one or more further MPNNs, wherein the further MPNNs are identically trained and configured as the first MPNN. This may be the case, for example, where the cost of obtaining processors is low, the desire for increased speed is high and/or it is advantageous to apply the MPNN to multiple variants simultaneously. Alternatively, a single MPNN may be provided and the variants analysed one after the other, with the outputs of the earlier analyses being buffered until the output of the subsequent analyses are available.

The system (100) may further comprise an encoder (107) functionally coupled to the input layer (103) of the MPNN so that biological sequences, which are discrete-symbol sequences, can be encoded numerically and used as inputs to the MPNN (101). It will be appreciated that the encoder may be applied in different ways and that an encoder may not be used at all. The encoder (107) may further encode the additional information to be input to the MPNN (101). Examples of additional information are context, cell type, tissue type, age, sex and combinations of these.

It may be advantageous for the system to comprise one or more further encoders, wherein the further encoders are identical to the first encoder. This may be the case, for example, where the cost of obtaining processors is low, the desire for increased speed is high and/or it is advantageous to apply the MPNN to multiple variants and additional informations simultaneously. Alternatively, a single encoder may be provided and the variants and additional informations analysed one after the other, with the outputs of the earlier analyses being buffered until the output of the subsequent analyses are available. It will be appreciated that the encoder may be applied in different ways and that an encoder may not be used at all.

One method that may be applied by the encoder (107) is to encode the sequence of symbols in a sequence of numerical vectors, a vector sequence, using, for example, one-hot encoding. The symbol $s_i$ is encoded in a numerical vector $x_i$ of length m: $x_i=(x_{i,1}, \ldots, x_{i,m})$ where $x_{i,j}=[s_i=\alpha_j]$ and $[\cdot]$ is defined such that [True]=1 and [False]=0 (so called Iverson's notation). One-hot encoding of all of the biological sequence elements produces an m×n matrix X. For example, a DNA sequence CAAGTTT of length n=7 and with an alphabet $\mathcal{A}=(A, C, G, T)$, such that m=4, would produce the following vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

Such an encoding is useful for representing biological sequences as numeric inputs to the neural network. It will be appreciated that other encodings of X may be computed from linear or non-linear transformations of a one-hot encoding, so long as the transformed values are still distinct.

With this method, the vector sequence is in correspondence with a matrix of substitution variants and corresponding reference symbols. The rows of X correspond to the different possible substitutions or reference symbols. Note that the locations of the 1's specify which symbols correspond to the reference symbols.

A comparator (112) may be provided at the output of the MPNN to compare the output Y (108) of MPNN (101) to a desired output or target, Y' (117). The molecular phenotype target may be ascertained using experimental techniques, such as RNA-Seq, ChIP-Seq, microarrays, RT-PCR, SELEX, and massively parallel reporter assays. This is useful for training, in which the neural network is configured using the parameters W such that, for input-target pairs (X, Y') in the training set of many such input-target pairs, the network's output Y=F(X; W) is a good approximation of the training target Y', across the input-output pairs in the training set. The error or cost (113) between the neural network output Y and a target Y' can be quantified by, for example, the squared error $(Y-Y')^2$. It will be appreciated that different error or cost functions may be used. The error term is incorporated into a loss function L(X, Y'; W), which measures the discrepancy between the output of the neural network and the desired output. In the example, $L(X, Y'; W)=(F(X; W)-Y')^2$. The process of training involves configuring W so as to minimize the total loss in a training set, such as the sum over the training examples of the loss for each example. Training may consist of determining a configuration W that minimizes or approximately minimizes the expected value or sum of L for pairs (X, Y') sampled from either training set or from a held-out validation set.

The MPNN may be operated in the back-propagation mode, which may be used to determine how changes in the intermediate computations, the inputs, and the parameters will impact the output (108) of the neural network. These three types of changes are referred to as gradients or derivatives and are denoted $\partial Y/\partial Z$, $\partial Y/\partial X$ and $\partial Y/\partial W$ respectively. Note that while Z is not explicit in the input-output relationship Y=F(X; W), the output depends on the intermediate computations and so the gradient of the output with respect to the values produced by the intermediate computations can be determined. These gradients are useful for training, but here we will also use the back-propagation mode for scoring biological sequence variations.

In the backward-propagation mode, an MPNN is a structured architecture that comprises a series of computations that starts with the output of the MPNN and works its way back to the input, so as to determine the gradients $\partial Y/\partial Z$, $\partial Y/\partial X$ and $\partial Y/\partial W$ for values produced by all of the intermediate computations Z, for all inputs X, and for all parameters W. First, the MPNN is operated in the forward-propagation mode to compute Y=F(X;W) (108). Then, in the back-propagation mode, the feature detectors are configured to act as gradient detectors. Each layer (102", 102', 102) of gradient detectors comprises the structured determination of the output of the gradient detectors (104), and each gradient detector (104) implements a computation that maps an input to an output. The gradient detectors (104) in a layer accept a plurality of inputs from subsequent layers in the architecture, combine them with a subset of weights, or parameters, W, and apply activation functions. Generally, the output of a gradient detector in layer l may be provided as input to one or more gradient detectors in layers l-1, l-2, . . . , 1. For example, in FIG. 1, outputs of gradient detectors (104) of layer (102") may be provided as input to one or more gradient detectors (104) of a plurality of previous layers (102' and 102), as shown by the dashed arrows. The output of the back-propagation mode is the output of the gradient detector at the input layer (103), which is the set of gradients $\partial Y/\partial X$ (114) for all inputs or a selected subset of inputs. For example, if the input comprises an m×n binary matrix representing a one-hot encoding of the biological sequence, the back-propagation mode may produce an m×n matrix of gradients corresponding to the reference symbols and variants. If the input also comprises additional information, such as a specification of the cell type, the derivatives for the cell type may not be output, but in this case the matrix of gradients corresponding to the reference symbols and variants provide information about the scores of the variants in the context of the provided cell type.

Embodiments described herein use the forward-propagation mode and the back-propagation mode to compute gradients for input symbols, including reference symbols and variants, using either the output itself, $\partial Y/\partial X$, or the loss function, $\partial L(X,Y';W)/\partial X$, and use these gradients to score and visualize the effects of variations in the biological sequence on molecular phenotypes. A scoring module (111) determines the scores of variants using the output determined using the back-propagation mode (114), the output determined using the forward-propagation mode (108), or both. A visualization module (116) applies the scores to generate a visualization of the effects of the variant on the molecular phenotype.

Figure 2:
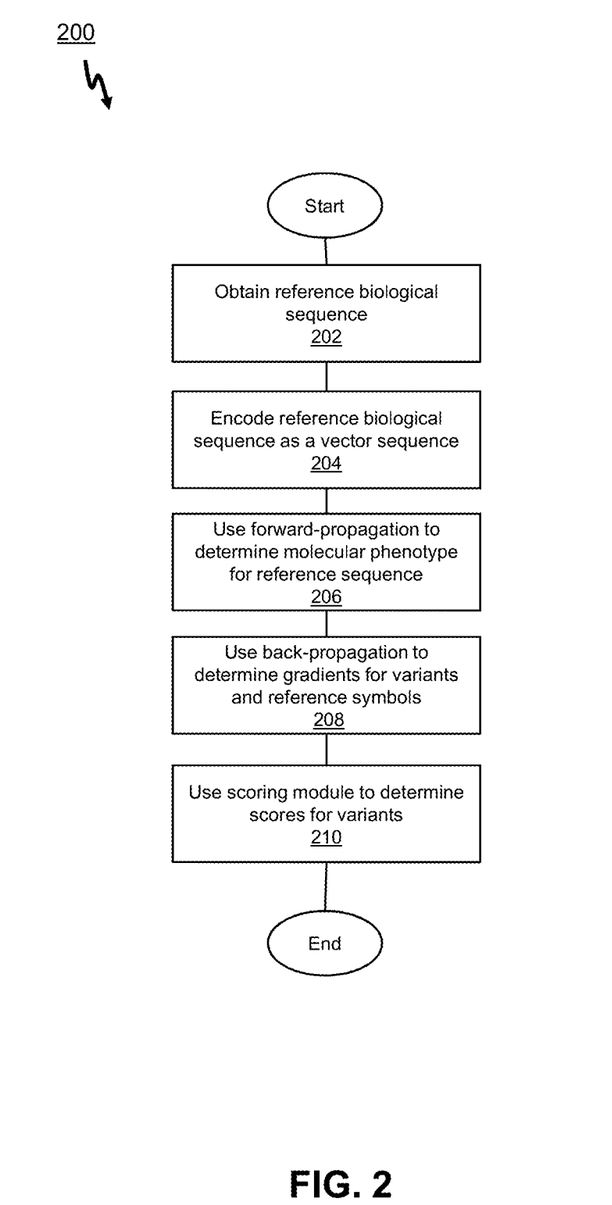
FIG. 2 shows an example flowchart of how the variant scores may be determined using the methods and systems described herein.

Referring now to FIG. 2, an exemplary flowchart illustrates a method (200) for determining variant scores. At block 202, a reference biological sequence is obtained and, at block 204, encoded by encoder (107) to produce a vector sequence. The encoder (107) may further encode additional information to be input to the MPNN. At block 206, the MPNN is operated in the forward-propagation mode to determine the molecular phenotype and at block 208 the MPNN is operated in the back-propagation mode to determine the gradients for the symbols at every position or a subset of positions in the vector sequence. At block 210, the gradients are used to determine the scores for the variants. The scores quantitatively characterize how the symbols are responsible for the output Y. For example, for a DNA vector sequence input X and a computed output Y, the gradients for every possible substitution in the DNA sequence can be used to identify mutations, sequence motifs, or combinations thereof that the output is sensitive to. A sequence of length n would have 4n gradients, which include the n gradients for the reference symbols and the 3n variants.

It will be appreciated that multiple biological sequences may be processed in parallel or sequentially by appropriately modifying the flowchart.

In one embodiment, the forward-propagation mode is used to determine the output (206) and then the back-propagation mode is used to determine the gradient $\partial Y/\partial x_{i,j}$ (208) for every symbol in the input vector sequence X, where $x_{i,j}$ corresponds to the symbol $\alpha_i$ at position j in the biological sequence. Note that gradient for $x_{i,j}$ depends on the entire current vector sequence X. Returning to the above example of a DNA sequence CAAGTTT of length n=7 and with an alphabet $\mathcal{A}$ =(A, C, G, T), such that m=4, the vector sequence, $$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix},$$

is fed into the neural network and the output is determined. Then, the back-propagation mode is used to compute numerical values for the gradients of the variants and the reference symbols, which can be viewed as a matrix of values in correspondence with the vector sequence:

$$\partial Y/\partial X = \begin{pmatrix} \partial Y/\partial x_{1,1} & \partial Y/\partial x_{2,1} & \partial Y/\partial x_{3,1} & \partial Y/\partial x_{4,1} & \partial Y/\partial x_{5,1} & \partial Y/\partial x_{6,1} & \partial Y/\partial x_{7,1} \\ \partial Y/\partial x_{1,2} & \partial Y/\partial x_{2,2} & \partial Y/\partial x_{3,2} & \partial Y/\partial x_{4,2} & \partial Y/\partial x_{5,2} & \partial Y/\partial x_{6,2} & \partial Y/\partial x_{7,2} \\ \partial Y/\partial x_{1,3} & \partial Y/\partial x_{2,3} & \partial Y/\partial x_{3,3} & \partial Y/\partial x_{4,3} & \partial Y/\partial x_{5,3} & \partial Y/\partial x_{6,3} & \partial Y/\partial x_{7,3} \\ \partial Y/\partial x_{1,4} & \partial Y/\partial x_{2,4} & \partial Y/\partial x_{3,4} & \partial Y/\partial x_{4,4} & \partial Y/\partial x_{5,4} & \partial Y/\partial x_{6,4} & \partial Y/\partial x_{7,4} \end{pmatrix}.$$

Note that in each column, one of the gradients corresponds to a reference symbol and the other gradients correspond to variants. For instance, in the example where the first symbol is a C and corresponds to a one-hot encoding with a 1 in the second row, the gradient $\partial Y/\partial x_{1,2}$ corresponds to the reference symbol, whereas the gradients $\partial Y/\partial x_{1,1}$, $\partial Y/\partial x_{1,3}$, and $\partial Y/\partial x_{1,4}$ correspond to the variants A, G, T.

It will be appreciated that if the variant gradients for only a subset of positions are needed, or for only a subset of variants at each position, or for only a subset of position-variant combinations, computations can be saved when operating the neural network in the back-propagation mode.

At block 210, the scoring module (111) determines a score for the variant in a way that depends on the gradients determined using the back-propagation mode (114), the molecular phenotype determined using the forward-propagation mode (108), or both. For example, the scoring module (111) may assign as a score the absolute value of the gradient, $|\partial Y/\partial x_{i,j}|$, an unsigned measure of the gradient. Note that these gradients depend on the output of the neural network Y, but they do not depend on the known target Y'. The gradient for a particular symbol $x_{i,j}$ in the context of the input vector sequence X is a characterization of to what degree, and in what way, the output Y is sensitive to the symbol $x_{i,j}$.

In another embodiment, there are multiple outputs (108) of the neural network. Different outputs may correspond to different molecular phenotypes. Different outputs may correspond to different conditions. Let $y_h$ denote the hth output of the neural network, so that $Y=(y_1, y_2, \ldots)$. Each variant can have different gradients for different outputs of the neural network. The neural network operating in back-propagation mode can be used to determine the gradient of output $y_h$ with respect to symbol $x_{i,j}$ and we denote this gradient by $\partial y_h/\partial x_{i,j}$. Here, for every output of the neural network, different gradients are ascertained for different variants in the input vector sequence. The absolute value of the gradient, $|\partial y_h/\partial x_{i,j}|$, may be used.

In another embodiment, the neural network operating in the back-propagation mode is used to determine gradients of the loss function, L(X, Y';W), which depends on the target Y'.

The MPNN examples described above may all be implemented by the same or possibly different MPNN structures;

that is, the number, composition and parameters of the nodes and layers may or may not differ. It will be appreciated that the biological sequences need not be of the same length and that an MPNN may be trained to account for other molecular phenotypes, for other biologically related variants and for other specifications of the additional information.

It will also be appreciated that many different machine learning architectures can be represented as neural networks, including linear regression, logistic regression, softmax regression, decision trees, random forests, support vector machines and ensemble models. Differences between techniques and architectures often pertain to differences in the cost functions and optimization procedures used to configure the architecture using a training set.

It will also be appreciated that the MPNN may also take as input a vector of features that are derived from the variant sequence. Examples of features include locations of protein binding sites, RNA secondary structures, chromatin interactions, and protein structure information.

We now describe details for determining the scores of substitutions from the gradients. It will be appreciated that there are different embodiments for ascertaining the gradients and the substitution scores that have the same result.

Consider the case where the output of the neural network Y is a single numerical output. It will be appreciated that multiple outputs can be addressed as described previously. The method produces a set of variant scores U that correspond to the variants in the vector sequence X; $u_{i,j}$ is the variant score corresponding to $x_{i,j}$. As a consequence of notational simplicity, the method produces variant scores for reference symbols, but it will be appreciated that these need not be examined, stored or computed. As above, the first step is to determine the gradients $\partial Y/\partial X$ by operating the neural network in forward-propagation mode and then in back-propagation mode. This produces the set of gradients, which is denoted $\Delta = \partial Y/\partial X$, and where the individual element $\Delta_{i,j} = \partial Y/\partial x_{i,j}$ corresponds to input symbol $x_{i,j}$.

In the embodiments described herein, the gradients $\partial Y/\partial X$ and the molecular phenotypes Y are fed into a scoring module (111), which determines the variant scores. This determination takes into account the application to biological sequences. The scoring module that takes into account the application to biological sequences is required, because the encoding of the biological sequence into a vector sequence yields vectors that are always normalized. Consequently, the raw gradients or their absolute values may not be indicative of the effect of a variation in the biological sequence. For example, for a particular position in the sequence, position i, the gradients for all variants may be positive: $\Delta_{i,j} > 0$, $\forall j \in \{1, \ldots, m\}$. However, the one-hot encoding requires that $\Sigma_{j=1}^{m} x_{i,j} = 1/m$ for m symbols. Consequently, in general, the largest gradient indicates that the corresponding symbol has a positive effect on the output, whereas the smallest gradient indicates that the corresponding symbol has a negative effect.

In one embodiment, the scoring module (111) uses the gradients $\partial Y/\partial X$ (114) but not the molecular phenotype Y (118), and the scoring module corrects for the one-hot encoding constraint described above. The variant scores are set to the gradients normalized by subtracting off the gradient for the reference symbol:

$$u_{i,j} \leftarrow \Delta_{i,j} - \Sigma_{j'=1}^{m} \Delta_{i,j'} x_{i,j'}.$$

This is equivalent to $$u_{i,j} \leftarrow \Delta_{i,j} - \Delta_i^*,$$

where $\Delta_i^*$ is the reference symbol gradient at position i.

In another embodiment, the scoring module additionally normalizes the scores so that the maximum absolute value across the symbols is one:

$$u_{i,j} \leftarrow u_{i,j}/(\max_{j'=1}^{m} |u_{i,j'}|).$$

In another embodiment, the scores are further normalized by dividing by the mean of the absolute values:

$$u_{i,j} \leftarrow u_{i,j} / \left( \frac{1}{m} \sum_{j'=1}^{m} |u_{i,j'}| \right).$$

In another embodiment, the absolute values of the scores are determined:

$$u_{i,j} \leftarrow |u_{i,j}|.$$

It will be appreciated that the scoring module may implement any combination of all of the above steps or a subset of these steps, and that they may be applied in different orders. For example, the variant scores may be set to the variant gradients, the reference gradients may be subtracted off and the scores normalized so that the maximum absolute value across the symbols is one.

Biological sequence variations may consist of large perturbations, such as from the vector (1, 0, 0, 0) encoding A to the vector (0, 1, 0, 0) encoding C. The gradient $\Delta_{i,j}$ linearly approximates the effects of large perturbations, so it may not be an accurate measure of the effect size. For example, if we observe a gradient $\Delta_{i,j} > 0$, it does not indicate that the output Y decreases proportionally, or even at all, with any substantial decrease in $x_{i,j}$; it is only suggestive of such a relationship. The relationship between $\Delta_{i,j}$ and the behavior of Y is especially tenuous for biological sequences, where a small perturbation in a symbol is not even a valid input, or where for a specific value of $x_{i,j}$ that deviates strongly from its background state, it may be in a saturated regime and thereby have a weak gradient, but the deviation nonetheless has a strong effect on the output value Y. Next, we describe embodiments that provide more accurate and useful variant scores in the application of biological sequence analysis.

Figure 3:
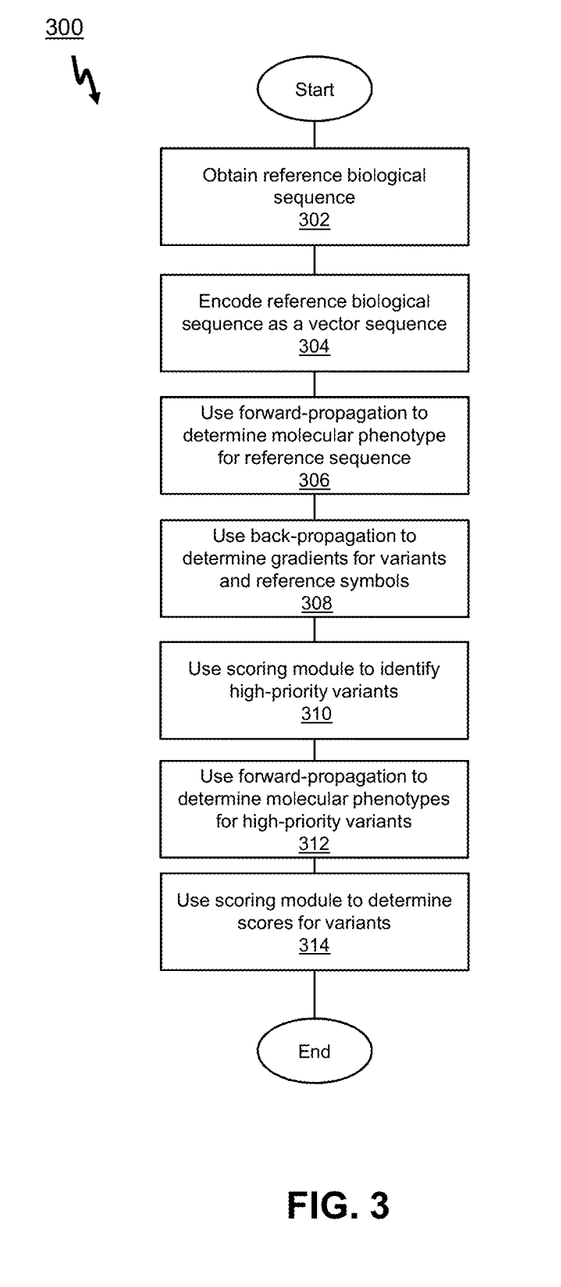
FIG. 3 shows another example flowchart of how the variant scores may be determined using the methods and systems described herein.

Referring now to FIG. 1, in another embodiment, the scoring module (111) uses the gradients $\partial Y/\partial X$ (114) to identify a subset of high-priority variants (118), which are evaluated by the MPNN to produce molecular phenotypes Y (118) that are used to produce scores by the scoring module (111). Referring now to FIG. 3, the reference biological sequence is obtained at block 302 and encoded at block 304. The MPNN is operated in the forward-propagation mode (306) and in the back-propagation mode (308) to determine the gradients for variants and reference symbols. The scoring module (111) uses the gradients to identify a subset of high-priority variants at block 310. At block 312, the high-priority variants are individually analyzed using the MPNN operating in forward-propagation mode. At block 314, the scoring module (111) combines the molecular phenotypes of the high-priority variants (108) and the gradients of the variants (114) to produce the variant scores. This method takes into account the larger and more realistic deviations in X described above. In one embodiment, at block 310, the scoring module identifies the indices of all variants whose variant gradients surpass a threshold. The threshold may be set to a fixed value based on a set of separate analyses, or it may be determined with respect to the set of scores as a whole, such as by determining a percentile threshold, which controls the computational budget for features that will be explicitly scored in the next step.

Denote by I the set of index pairs (i,j) that pass the threshold. Recall that i indexes position in the sequence and j indexes the symbol alphabet. At block 312, the scoring module (111) computes, separately and independently for each (i,j)∈I, the score of that particular sequence variant by using the molecular phenotype neural network in feed-forward mode. To do this, all effect scores $u_{i,j}$ for which (i,j)∈I are set to zero. Otherwise, for each particular (i,j)∈I, the method modifies the original vector sequence X by setting $x_{i,j}$=1 and $x_{i,j'}$=0 for j'≠j. The modified vector sequence is denoted $X^{(i,j)}$. The output $Y^{(i,j)}$=F($X^{(i,j)}$; W), corresponding to the modified input, is computed by operating the neural network in the forward-propagation mode. The variant score is then set as follows:

$$u_{i,j} \leftarrow Y^{(i,j)} - Y.$$

It will be appreciated that different embodiments comprise different combinations of the above techniques for normalizing the variant scores $u_{i,j}$. These include the following further modifications of the variant scores: $u_{i,j} \leftarrow u_{i,j}/(\max_{j'=1}^{m}|u_{i,j'}|)$;

$$u_{i,j} \leftarrow u_{i,j} \bigg/ \left(\frac{1}{m}\sum_{j'=1}^{m}|u_{i,j'}|\right);$$

$u_{i,j} \leftarrow |u_{i,j}|$. It will be appreciated that any subset of these may be applied and that the subset of steps may applied in a different order.

It will be appreciated that the original vector sequence can be modified in different ways, including replacing all values in the vector $x_i$ with the mean or the median of the corresponding values in a reference set; and if the reference set is known to be unbalanced, a skewed percentile-based threshold (rather than the median); or a weighted mean over the same.

It will be appreciated that many of the intermediate computations produced during forward-propagation in the neural network can be stored and reused in memory (106), reducing computational costs. For example, the intermediate computations produced during forward-propagation applied to the reference variant sequence can be stored and then, when a one of the inputs to the neural network is changed to account for a substitution, only the intermediate computations that depend on that input need to be recomputed.

It will be appreciated that many of the intermediate computations produced during back-propagation in the neural network can be stored and reused in memory (106), reducing computational costs.

In one embodiment, to account for cases where some features are highly correlated with one another, the substituted value can be determined using the values for $x_{i,j}$ found in other training cases or test cases that have similar values for $x_{i',j}$, i'≠i.

In another embodiment, variants in biological sequences that have the form of deletions can be evaluated to determine their scores. A deletion is the removal of one or more elements in a reference biological sequence. First, the reference sequence is encoded into an input vector sequence X. Then, the neural network is operated in forward-propagation mode to determine the output Y. Next, vectors in the vector sequence that correspond to the deleted elements are removed from the vector sequence, producing the modified vector sequence $X^d$. For example, a DNA sequence CAAGTTT of length n=7 and with an alphabet $\mathcal{A}$=(A, C, G, T), such that m=4, would have the following encoded vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

If the first and fourth elements are deleted, producing the sequence AATTT, the vector sequence is modified as follows:

$$X^d = \begin{pmatrix} 1 & 1 & 0 & 0 & 0 \\ 0 & 0 & 0 & 0 & 0 \\ 0 & 0 & 0 & 0 & 0 \\ 0 & 0 & 1 & 1 & 1 \end{pmatrix}.$$

Next, the modified vector sequence is fed into the neural network, which is operated in the feed-forward mode to produce an output $Y^d$. The difference in the outputs is the variant score: $u \leftarrow Y^d - Y$. It will be appreciated that this score may be modified in different ways to product useful variant scores, such as the absolute value: $u \leftarrow |Y^d - Y|$.

In another embodiment, all possible single-element deletions in the reference biological sequence are determined using the above method. For a sequence of length n, this will take n applications of the method described above.

In another embodiment, the scores of variants in the reference sequence that have the form of insertions are determined. An insertion comprises extending the sequence by inserting one or more symbols at various positions in the sequence. First, the reference sequence is encoded into an input vector sequence X. Then, the neural network is operated in forward-propagation mode to determine the output Y. Next, vectors are inserted into the vector sequence that correspond to the inserted elements, producing the modified vector sequence X. For example, a DNA sequence CAAGTTT of length n=7 and with an alphabet $\mathcal{A}$=(A, C, G, T), such that m=4, would have the following encoded vector sequence:

$$X = \begin{pmatrix} 0 & 1 & 1 & 0 & 0 & 0 & 0 \\ 1 & 0 & 0 & 0 & 0 & 0 & 0 \\ 0 & 0 & 0 & 1 & 0 & 0 & 0 \\ 0 & 0 & 0 & 0 & 1 & 1 & 1 \end{pmatrix}.$$

If the symbol A is inserted before the first element in the sequent and the symbol C is inserted before the fifth symbol in the sequence, the biological sequence becomes ACAAGCTTT and the following modified vector sequence is produced:

$$X^s = \begin{pmatrix} 1 & 0 & 1 & 1 & 0 & 0 & 0 & 0 & 0 \\ 0 & 1 & 0 & 0 & 0 & 1 & 0 & 0 & 0 \\ 0 & 0 & 0 & 0 & 1 & 0 & 0 & 0 & 0 \\ 0 & 0 & 0 & 0 & 0 & 0 & 1 & 1 & 1 \end{pmatrix}.$$

Next, the modified vector sequence is fed into the neural network, which is operated in the feed-forward mode to produce an output $Y^s$. The difference in the outputs is the variant score: $u \leftarrow Y^s - Y$. It will be appreciated that this score may be modified in different ways to product useful variant scores, such as the absolute value: $u \leftarrow |Y^s - Y|$.

In another embodiment, all possible single-element insertions in the reference biological sequence are determined using the above method. For a sequence of length n and alphabet size m, this will take n(m−1) applications of the method described above.

The gradient method can be extended to second order derivatives so that all combinations {i, i', j, j'} such that $\partial F(X;W)/(\partial x_{i,j} \partial x_{i',j'})$ is above a threshold can be selected for evaluating their combined effect score, where $u_{i,j} = |Y^{(i,j)} - Y|$ is calculated from $Y^{\{i,i',j,j'\}} = F(X^{\{i,i',j,j'\}}; W)$ for those {i, i', j, j'} that pass the threshold.

In another embodiment, the thresholding method described above and shown in FIG. 3 is adapted by implanting scoring module (111) by a second neural network $U = G(X, Y, \Delta; V)$ that takes as input the original vector sequence X, the output Y of the neural network applied to that sequence, and the variant gradients $\Delta$. We refer to this as a scoring module neural network, G.

The scoring module neural network G is trained to output the matrix of variant scores U. Datasets that may be used for this purpose include massively parallel reporter assay datasets, clinical datasets and SELEX datasets. Here the architecture of G and its parameters V are not related to the original neural network F and its parameters W. The MPNN (101) is used to produce Y and $\Delta$, which are then used separately to train the scoring module neural network. This embodiment can be important in scenarios where a variant deviates so much from its background value that it is in a saturated regime of F and therefore has small gradient. In this embodiment, if we set $G = \Delta$ rather than training the scoring module neural network, then the method reduces to the thresholding method.

In another embodiment, G uses a subset of the features. In a particular embodiment, the scoring module neural network has the form $G(\Delta; V)$, which is generally more accurate than using the thresholding method where $G = \Delta$.

In another embodiment, the variant scores obtained using one of the methods described herein are further used to produce a visualization. The visualization provides an informative readout for diagnosticians, pharmaceutical researchers and other users of the variant effect score information.

Figure 4:
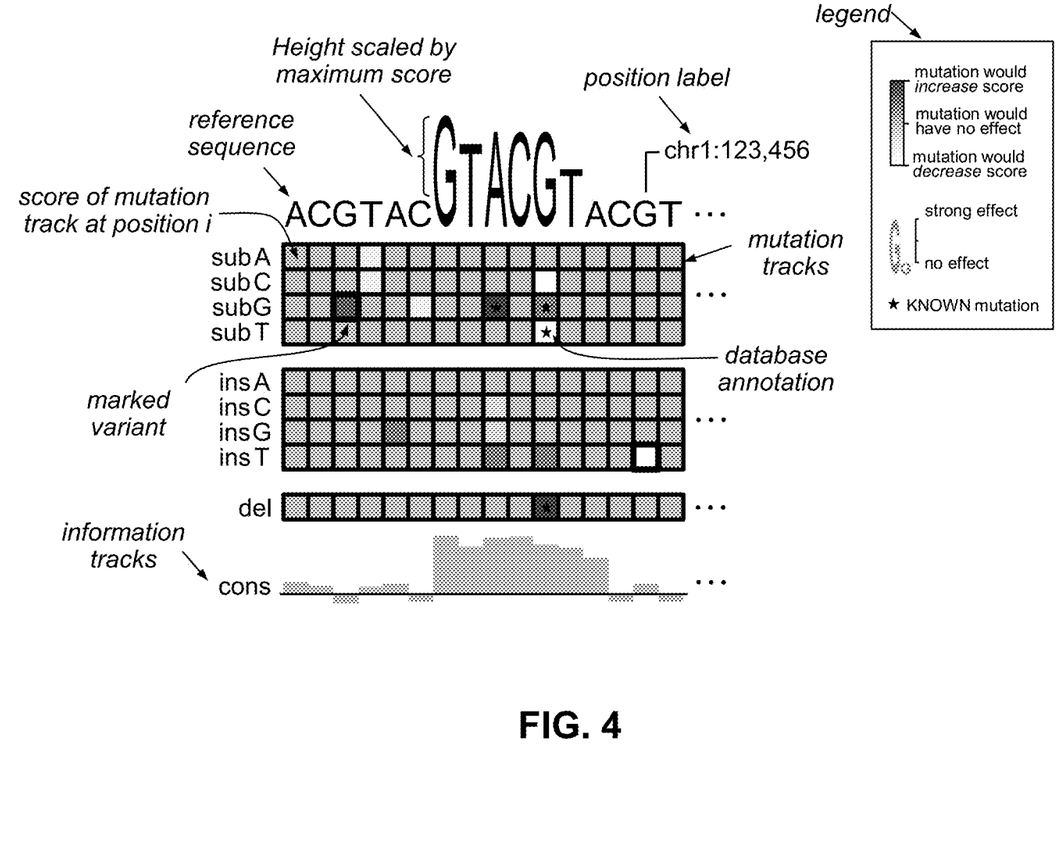
FIG. 4 shows a first example visualization.

Referring now to FIG. 4, shown therein is an example of the visualization produced by the visualization module (116) in this embodiment, using an example of a reference DNA sequence (m=4) of length n=16: ACGTACGTACGTACGT (SEQ ID NO: 1). The embodiments described above are used to determine the substitution scores, the insertion scores and the deletion scores for all possible single-element substitutions, insertions and deletions. These scores may be signed or unsigned. For visualization, the reference sequence is written and the three types of scores are visually represented as an aligned set of mutation tracks (see FIG. 3). Each mutation track corresponds to a type of variant (substitution, insertion or deletion) and in the case of substitutions and insertions is also associated with a particular symbol from the alphabet. The mutation tracks represent variants using visually distinctive elements, such as through the use of black and white, greyscale or color elements that encode the numerical values of the corresponding variant scores.

To indicate the importance of each symbol in the reference sequence, the visualization module (116) scales the height of the symbol by the maximum variant score for that position in the sequence. The maximum variant score may be determined by examining the scores for substitutions; or the scores for insertions; or the scores for deletions; or the scores for any combination of substitutions, insertions and deletions, where each type of variant may be weighted differently. The maximum variant score may be determined using absolute values of the variants scores.

The variant scores are visually represented in the mutation tracks using a colormap that indicates the variant score value. The colormap may be grayscale, or it may use many colors. The colormap may indicate the sign of the score as well as its magnitude, or it may indicate the absolute value of the score. Different types of variants (substitutions, insertions, deletions) may use the same colormap or they may have different colormaps.

As shown in FIG. 4, the visualization module (116) may align additional information tracks, such as conservation, allele frequency, or ChIP-Seq tracks, with the reference sequence to convey supporting information pertaining to the variant scores.

Also as shown in FIG. 4, the visualization module (116) may include annotations of some or all mutations using symbols that are placed within the mutation tracks, such as symbols indicating mutations that have been previously associated with a disease of interest. A legend may be included that indicates the meaning of the annotation symbols. There may be more than one such type of annotation and different symbols or the same symbol may be used to indicate the more than one such type of annotation. Variants may be further marked by drawing bold boxes around the corresponding elements in the mutation tracks.

Additional information providing context may be included, such as an indication of where the reference sequence or elements from the reference sequence come from in other sequence databases, such as in the human genome. FIG. 4 shows an example, wherein an element is associated with location 123,456 in chromosome 1 of the human genome.

Figure 5:
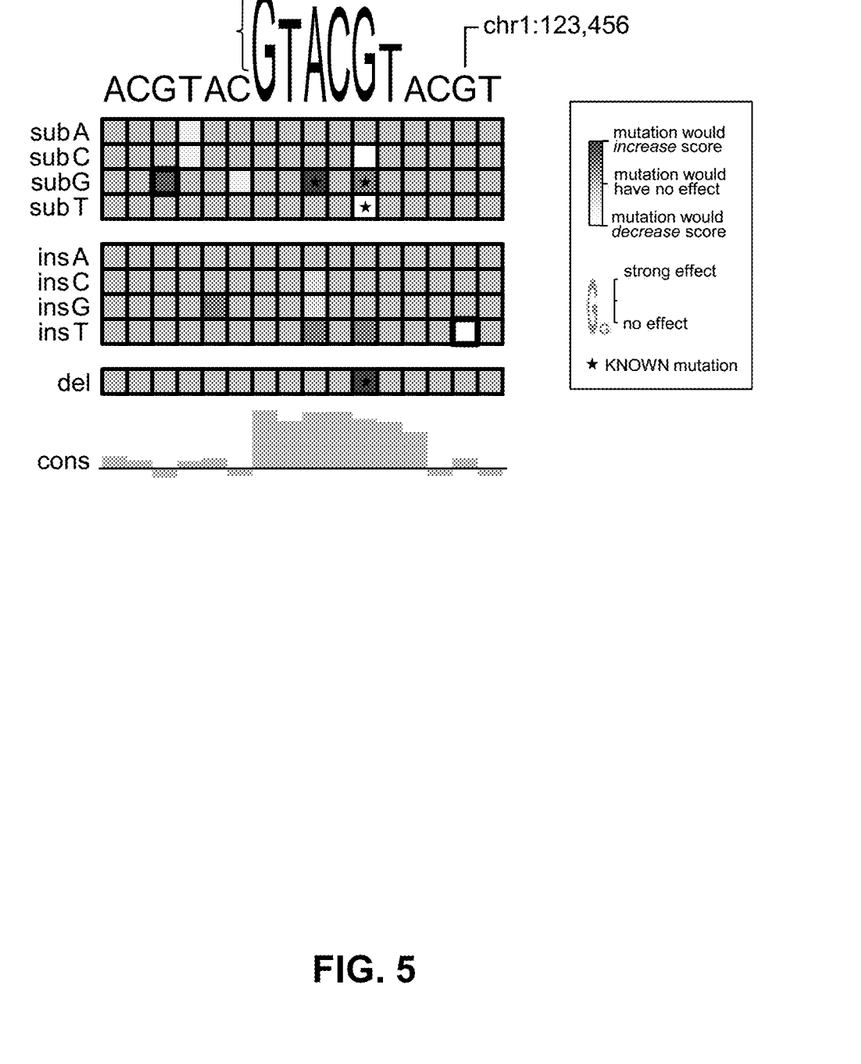
FIG. 5 shows a second example visualization, FIG. 5 discloses SEQ ID NO: 1.

It will be appreciated that not all labels shown in FIG. 4 need to be shown in the visualization. FIG. 5 shows an example, wherein several labels, such as "mutation tracks", have been removed.

Figure 6:
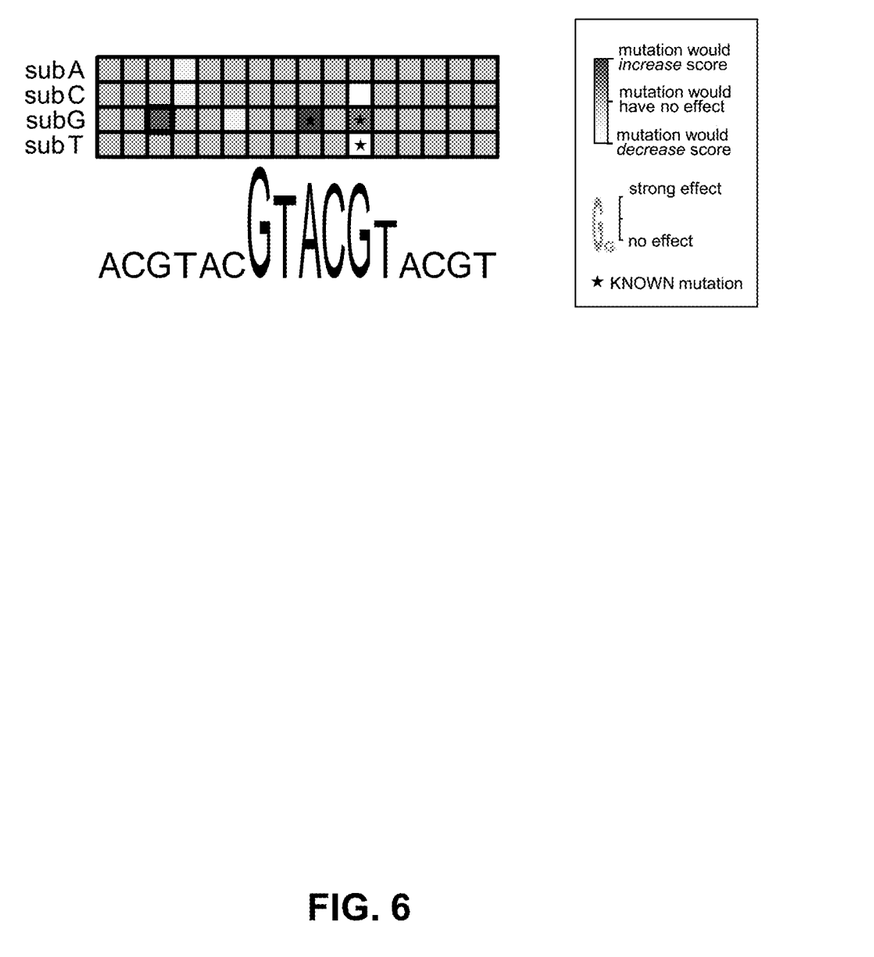
FIG. 6 shows a third example visualization.

It will be appreciated that the reference biological sequence, the mutation tracks and the information tracks may be shown in different vertical orders, and some tracks may not be shown, although at least one variant score track must be shown. FIG. 6 shows an example having at least one variant score track shown. It will be appreciated that tracks that are not shown need not be computed.

Although the invention has been described with reference to certain specific embodiments, various modifications thereof will be apparent to those skilled in the art without departing from the spirit and scope of the invention as outlined in the claims appended hereto.

The invention claimed is:

1. A method for determining a variant score for a set of substitution variants at each of one or more variant positions in a reference biological sequence using a molecular phenotype neural network (MPNN), the reference biological sequence characterized by a sequence of reference symbols, the method comprising:
  obtaining at an input layer of the MPNN the reference biological sequence;
  obtaining at the input layer of the MPNN a set of variant biological sequences comprising modifications of the reference biological sequence by the set of substitution variants, each of the set of substitution variants associated with a variant position in the reference biological sequence;
  operating the MPNN in a forward-propagation mode to determine a molecular phenotype for the reference biological sequence and variant molecular phenotypes for the set of variant biological sequences, wherein the molecular phenotype for the reference biological sequence and the variant molecular phenotypes for the set of variant biological sequences each comprises values which quantify aspects of biological molecules of cells;
  operating the MPNN in a back-propagation mode to determine a gradient for each of the set of substitution variants and for each of the set of substitution variants, a gradient for the reference symbol at a respective variant position in the reference biological sequence; and
  for each of the set of substitution variants, determining a variant score at least in part by comparing, using a comparator, the gradient for the substitution variant and the gradient for the reference symbol at the respective variant position in the reference biological sequence.

2. The method of claim 1, further comprising using an encoder to encode the reference biological sequence prior to operating the MPNN, the encoder generating a reference vector sequence encoding the reference biological sequence.

3. The method of claim 1, wherein the comparing further comprises subtracting the gradient for the reference symbol at the respective variant position in the reference biological sequence from the gradient for the substitution variant.

4. The method of claim 1, wherein the comparing further comprises, for each of the set of substitution variants, if the variant score is greater than a pre-determined threshold:
  obtaining a variant biological sequence representing the reference biological sequence modified by the substitution variant at the associated variant position in the reference biological sequence;
  operating the MPNN in the forward-propagation mode to determine a molecular phenotype for the variant biological sequence; and
  comparing the molecular phenotype for the variant biological sequence and the molecular phenotype for the reference biological sequence.

5. The method of claim 4, wherein comparing the molecular phenotype for the variant biological sequence and the molecular phenotype for the reference biological sequence further comprises subtracting the molecular phenotype for the reference biological sequence from the molecular phenotype for the variant biological sequence.

6. The method of claim 1, wherein operating the MPNN in the back-propagation mode to determine the gradient for each of the set of substitution variants further comprises comparing outputs of the MPNN to a pre-determined target.

7. The method of claim 1, wherein determining the variant score further comprises determining an absolute value of a difference between the gradient for the substitution variant and the gradient for the reference symbol at the respective variant position.

8. The method of claim 1, wherein determining the variant score further comprises:
  determining variant scores for all substitution variants at the associated variant position in the reference biological sequence; and
  dividing the variant score by a maximum absolute value of the variant scores for all substitution variants at the associated variant position in the reference biological sequence.

9. The method of claim 1, wherein determining the variant score further comprises operating a scoring module neural network in a feed-forward mode, wherein an input of the scoring module neural network comprises: the gradient for the substitution variant and gradients for all other symbols at the respective variant position in the reference biological sequence.

10. A system for determining a variant score for a set of substitution variants at each of one or more variant positions in a reference biological sequence, the reference biological sequence characterized by a sequence of reference symbols, the system comprising:
  a module configured to obtain a reference biological sequence and a set of substitution variants, each of the set of substitution variants associated with a variant position in the reference biological sequence;
  a molecular phenotype neural network (MPNN) for determining a molecular phenotype for a biological sequence, the MPNN comprising an input layer for obtaining the reference biological sequence and a set of variant biological sequences comprising modifications of the reference biological sequence by the set of substitution variants, each of the set of substitution variants associated with a variant position in the reference biological sequence, wherein the MPNN operates in a forward-propagation mode to determine a molecular phenotype for the reference biological sequence and variant molecular phenotypes for the set of variant biological sequences, wherein the molecular phenotype for the reference biological sequence and the variant molecular phenotypes for the set of variant biological sequences each comprises values which quantify aspects of biological molecules of cells, wherein the MPNN operates in a back-propagation mode to determine a gradient for each of the set of substitution variants and for each of the set of substitution variants, a gradient for the reference symbol at a respective variant position in the reference biological sequence; and a comparator for determining a variant score for each of the set of substitution variants at least in part by comparing the gradient for the substitution variant and the gradient for the reference symbol at the respective variant position in the reference biological sequence.

11. The system of claim 10, wherein the system further comprises an encoder for encoding the reference biological sequence prior to operating the MPNN, the encoder generating a reference vector sequence encoding the reference biological sequence.

12. The system of claim 10, wherein the comparing further comprises subtracting the gradient for the reference symbol at the respective variant position in the reference biological sequence from the gradient for the substitution variant.

13. The system of claim 10, wherein the comparing further comprises, for each of the set of substitution variants, if the variant score is greater than a pre-determined threshold:

obtaining a variant biological sequence representing the reference biological sequence modified by the substitution variant at the associated variant position in the reference biological sequence;

operating the MPNN in the forward-propagation mode to determine a molecular phenotype for the variant biological sequence; and comparing the molecular phenotype for the variant biological sequence and the molecular phenotype for the reference biological sequence.

14. The system of claim 13, wherein comparing the molecular phenotype for the variant biological sequence and the molecular phenotype for the reference biological sequence further comprises subtracting the molecular phenotype for the reference biological sequence from the molecular phenotype for the variant biological sequence.

15. The system of claim 10, wherein operating the MPNN in the back-propagation mode to determine the gradient for each of the set of substitution variants further comprises comparing outputs of the MPNN to a pre-determined target.

16. The system of claim 10, wherein determining the variant score further comprises determining an absolute value of a difference between the gradient for the substitution variant and the gradient for the reference symbol at the respective variant position.

17. The system of claim 10, wherein determining the variant score further comprises:

determining variant scores for all substitution variants at the associated variant position in the reference biological sequence; and dividing the variant score by a maximum absolute value of the variant scores for all substitution variants at the associated variant position in the reference biological sequence.

18. The system of claim 10, wherein determining the variant score further comprises operating a scoring module neural network in a feed-forward mode, wherein an input of the scoring module neural network comprises: the gradient for the substitution variant and gradients for all other symbols at the respective variant position in the reference biological sequence.

* * * * *